(12) United States Patent
Manca et al.

(10) Patent No.: US 7,479,556 B2
(45) Date of Patent: Jan. 20, 2009

(54) PROCESS FOR PRODUCING CEFEPIME AND CEPHALOSPORIN ANALOGUES

(75) Inventors: Antonio Manca, Milan (IT); Riccardo Monguzzi, Dorio (IT); Maurizio Zenoni, Paullo (IT); Leonardo Marsili, Padenghe sul Garda (IT)

(73) Assignee: ACS Dobfar S.p.A., Tribiano (IT)

( * ) Notice: Subject to any disclaimer, the term of this patent is extended or adjusted under 35 U.S.C. 154(b) by 454 days.

(21) Appl. No.: 11/221,751

(22) Filed: Sep. 9, 2005

(65) Prior Publication Data

US 2006/0100424 A1    May 11, 2006

(30) Foreign Application Priority Data

Nov. 8, 2004  (IT) ................ MI2004A2139

(51) Int. Cl.
*C07D 501/06*    (2006.01)

(52) U.S. Cl. ............... 540/222; 540/224; 540/225

(58) Field of Classification Search ........... 540/224, 540/222, 225
See application file for complete search history.

(56) References Cited

U.S. PATENT DOCUMENTS

| 6,919,449 | B2 | 7/2005 | Deshpande et al. | |
| 2005/0043531 | A1* | 2/2005 | Handa et al. | 540/224 |
| 2005/0080070 | A1* | 4/2005 | Deshpande et al. | 514/202 |
| 2005/0119478 | A1 | 6/2005 | Monguzzi et al. | |
| 2006/0135761 | A1* | 6/2006 | Datta et al. | 540/222 |
| 2007/0105830 | A1* | 5/2007 | Ludescher et al. | 514/202 |

FOREIGN PATENT DOCUMENTS

WO    WO 2004092183 A2 * 10/2004
WO    WO 2006067803 A1 *  6/2006

* cited by examiner

*Primary Examiner*—Mark L Berch
(74) *Attorney, Agent, or Firm*—Oblon, Spivak, McClelland, Maier & Neustadt, P.C.

(57) ABSTRACT

Process for producing Cefepime, Cefpirome and Cefquinome, whereby a cephalosporin containing a quaternary ammonium group is reacted with thiourea to provide the aforesaid cephalosporins.

13 Claims, No Drawings

PROCESS FOR PRODUCING CEFEPIME AND CEPHALOSPORIN ANALOGUES

CROSS REFERENCE TO RELATED APPLICATION

This application claims priority under 35 U.S.C. § 119 to Italian Patent Application No. MI2004A 002139, filed Nov. 8, 2004.

BACKGROUND OF THE INVENTION

1. Field of the Invention

The present invention relates to a process for preparing Cefepime and cephalosporin analogues, i.e. Cefpirome and Cefquinome.

2. Discussion of the Background Art

U.S. patent application Ser. No. 10/916,532, filed on Aug. 12, 2004 (which is a continuation of U.S. patent application Ser. No. 10/821,986 filed on Apr. 12, 2004) describes a process for preparing cephalosporins of formula

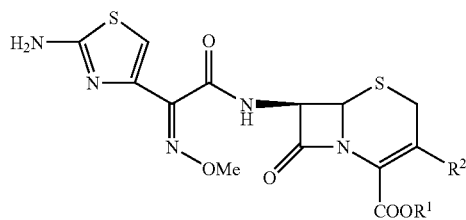

(II)

characterised by a 2-(2-aminothiazol-4-yl)-2-methoxyiminoacetic chain in the 7-position of 7-ACA and its derivatives of formula

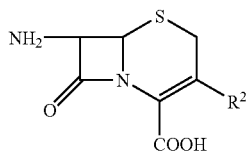

(I)

in which $R^2$ can have different meanings including $CH_2OCOCH_3$ for 7-ACA, being the cefotaxime nucleus, or

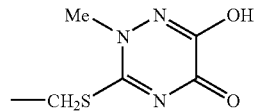

for 7-ACT, being the ceftriaxone nucleus and

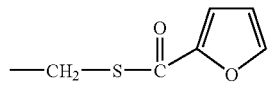

for Furaca, being the ceftiofur nucleus.

In said application, the synthesis takes place in two passages: the first consists of preparing an intermediate of formula

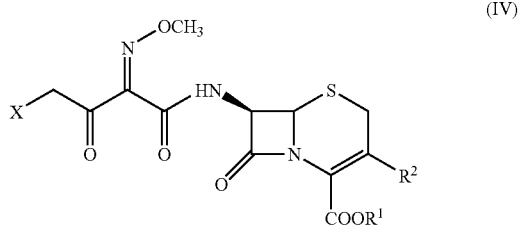

(IV)

by reacting a compound of formula (I)

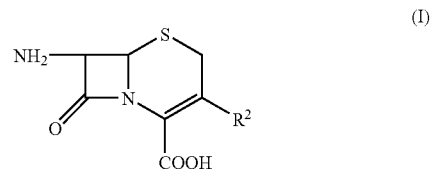

(I)

suitably silylated, with a compound of formula (V)

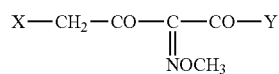

in which X is Cl or Br, Y is Cl, or $O—CH═N^+(CH_3)_2Cl^-$, isolating a compound of aforegiven formula (IV) in which X is Cl or Br and the carboxyl is salified with benzathine.

This procedure has however proved inapplicable in the case of compounds of formula (IV) containing a strongly basic substituent $R^2$ of the following type:

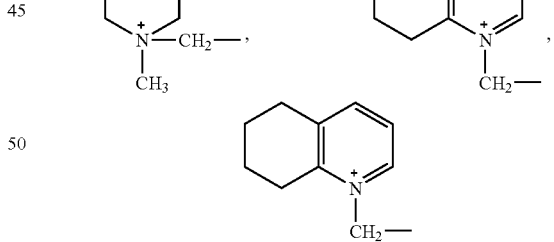

In this respect the aforesaid basic group $R^2$ forms an internal salt with the carboxyl group in the 4-position, which is hence present as $COO^-$ and does not enable the benzathine to salify the carboxyl.

This assertion is confirmed, for example, by US Patent Application 2003/0199712 in which a process is claimed (claim 5) for preparing a compound of formula (II) by passing via a compound similar to that of formula (IV), but in which the carboxyl can be a carboxylate ion, while the substituent in the 3-position can have one of the three aforesaid meanings for $R^2$, thus giving rise to an internal salt between the carboxylate ion and the basic group indicated as $R^2$.

It is therefore evident that the presence of the strongly basic group in the 3-position, in the case of the compound of formula (IV), gives rise to an internal salt, at least according to the expectations of one skilled in the art, while the benzathine salt alternative has proved to be impractical.

SUMMARY OF THE INVENTION

It has now been surprisingly found that a compound of formula

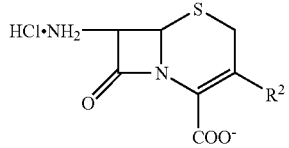
(III)

suitably silylated, in which $R^2$ is one of the three aforesaid substituents, can be reacted with a compound of formula (V)

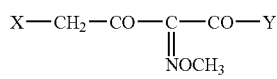

in which X is Cl or Br, Y is Cl, or $O-CH=N^+(CH_3)_2Cl^-$, in order to isolate a compound of formula

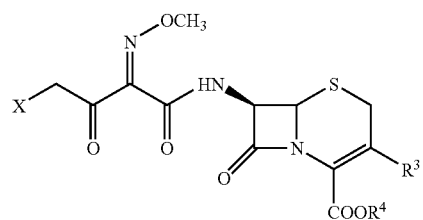
(VI)

in which $COOR^4$ is not in the form of a carboxylate ion but rather is simply COOH, while the substituent $R^3$ in the 3-position is of the following type:

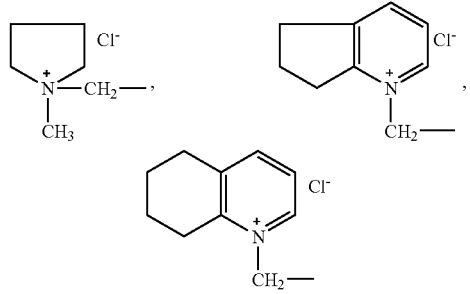

i.e. a quaternary ammonium group accompanied by a chloride anion.

The aforesaid compound of formula (VI) is therefore a quaternary ammonium salt which can be isolated in pure form by separating it from the reaction impurities and subsequently reacted with thiourea to produce a salt of a compound of formula (II) in which $COOR^1$ is $COO^-$ and $R^2$ is one of the following three substituents,

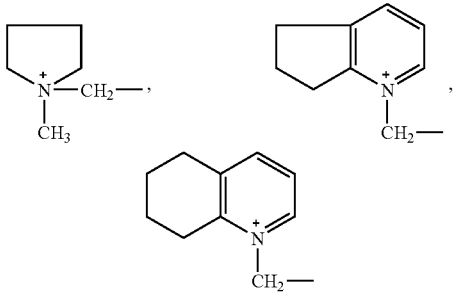

as reported in the Merck Index XIII Ed. for Cefepime, Cefpirome and Cefquinome. The salt of said compound, again according to the Merck Index XIII Ed., can be a hydrochloride or a sulfate in the case of Cefepime and a sulfate in the case of Cefpirome and Cefquinome.

DETAILED DESCRIPTION OF THE PREFERRED EMBODIMENTS

The invention relates therefore to a process for preparing a pharmaceutically acceptable salt chosen from the group consisting of a hydrochloride or a sulfate of a compound of formula (II) in which $COOR^1$ is a carboxylate ion and $R^2$ is chosen from the group consisting of

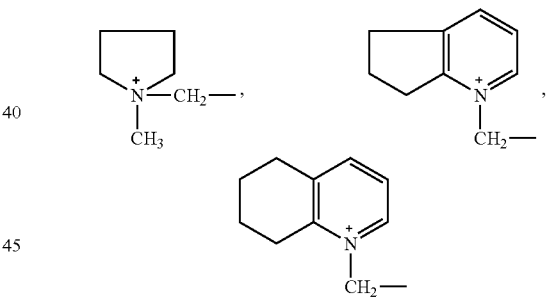

and also relates to a compound of formula (VI) in which X is Cl or Br; $R^4$ is H and $R^3$ is chosen from the group consisting of

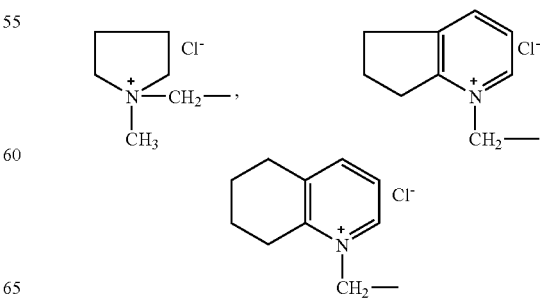

EXAMPLES

Example 1

Preparation of the Compound of Formula VI

7-[4-chloro-3-oxo-2-methoxyiminobutanoyl]amino]-2-carboxy-8-oxo-5-thia-1-azabicyclo[4.2.0]oct-2-ene-3-methyl-(1-methylpyrrolidinium)chloride Two separate solutions are prepared.

Solution A:

4g of (6R,7R)-7-amino-3-(1-methyl-1-pyrrolidinium)methyl-ceph-3-em-4-carboxylate hydrochloride (compound of formula III) (M.W. 333.92) are suspended in 150 ml of acetonitrile and cooled to +10° C. 0.1 ml of methanesulfonic acid are added followed by 8.6 g of N,O-bistrimethyl-silyl-acetamide (M.W. 203.43) allowing the temperature to rise spontaneously and freely. The mixture is stirred for 90 minutes at +33/+35° C. until a solution forms, and then cooled to −40° C.

Solution B:

1.4 ml of N,N-dimethylformamide are added to 30 ml of acetonitrile, the temperature is brought to +25° C., then after allowing it to rise to +36° C. 1.6 ml of phosphorus oxychloride (M.W. 153.33- d=1.675) are added. The mixture is stirred for 15-20 minutes at +36° C., then cooled to 0° C., to which 2.9 g of 4-chloro-3-oxo-2-methoxyimino-butyric acid, commonly known as COMBA (M.W. 179.56), are added without allowing the temperature to exceed +5° C. The mixture is agitated for 1 hour at 0° C./+5° C.

Solution B is poured into solution A over 15 minutes, while maintaining the temperature at −35/−40° C., it is agitated for 15-20 minutes and the reaction goes to completion. The reaction contents are poured into 50ml of wet isopropanol previously cooled to 0° C./−5° C. The temperature is raised to +25/+30° C. and the acetonitrile is evaporated under reduced pressure The product is taken up 3 times with 20 ml of isopropanol, and finally made up to a total volume of 100 ml with isopropanol. After cooling to 0° C. and stirring at this temperature for 1 hour, the mixture is filtered and the product washed twice with 20 ml of isopropanol. It is dried and 5.8 g (yield 98%) of the compound of formula (VI) are obtained, presenting the following spectrum:

$^1$H NMR (DMSO-d6, 300 MHz): 9.54, (1H, d); 5.90, (1H, dd); 5.29, (1H, d); 4.86, (2H, s); 4.60 and 4.24, (2H, AB system, $J_{AB}$=13.5 Hz); 4.05, (3H, s); 4.00 and 3.63, (2H, AB system, $J_{AB}$=17 Hz); 3.60, (3H, m); 3.43, (1H, m); 2.92, (3H, s); 2.11, (4H, m).

Example 2

Preparation of Cefepime Hydrochloride Monohydrate 5.8 g of the compound of formula (VI) obtained in Example 1 are suspended in 50 ml of water at +20/+25° C. 1.8 g of thiourea are added, the temperature is maintained at +20/+25° C., 5.9 g of sodium acetate are added and the mixture is stirred at this temperature for 3 hours. On termination of the reaction 240 ml of acetone are added. 35% hydrochloric acid is added at +20/+25° C. until pH 1.5 is attained. A further 360 ml of acetone are added dropwise over 1 hour, then the mixture is stirred for 30 minutes at +20/+25° C., cooled to 0° C. and stirred for 1 hour. The mixture is filtered and the product washed with 250 ml of acetone, then dried at +30° C. under reduced pressure. 6.3 g (93% yield) of Cefepime hydrochloride monohydrate are obtained, presenting the following spectrum:

$^1$H NMR (DMSO-d6, 300 MHz): 9.8, (1H, d); 6.8, (1H, s); 5.85, (1H, dd); 5.36, (1H, d); 4.6 and 4.4, (2H, AB system, $J_{AB}$=14 Hz); 4.1 and 3.7, (2H, AB system, $J_{AB}$=17 Hz); 3.9, (3H, s); 3.62, (3H, m); 3.46, (1H, m); 2.96, (3H, s); 2.1, (4H, m).

Example 3

Preparation of Cefepime Sulfate 5.8 g of the compound of formula (VI) obtained in Example 1 are suspended in 25 ml of water at +20° C./+25° C. 1.8 g of thiourea are added, the temperature is maintained at +20/+25° C., 5.9 g of sodium acetate are added and the mixture is stirred for 3 hours at +20/+25° C. On termination of the reaction 90 ml of acetone are added.

The solution is cooled to 0°/+5° C. then brought to pH 1.8 with a solution consisting of 30% H$_2$SO$_4$ and acetone (1:2.5 v:v).

The solution is then stirred for 1 hour, filtered, washed with 50 ml of acetone and dried under reduced pressure at +30° C. 4.8 g (yield 72%) of Cefepime sulfate are obtained whose $^1$HNMR spectrum coincides with that of Cefepime hydrochloride.

By applying the same method to compounds of formula (III) in which R$^2$ is chosen from the following group

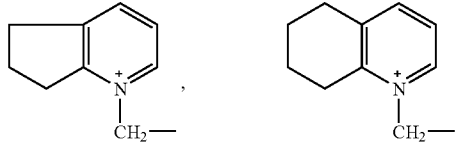

Cefpirome sulfate is obtained in the first case and Cefquinome sulfate in the second case.

What is claimed is

1. A process for preparing a compound of formula (VI):

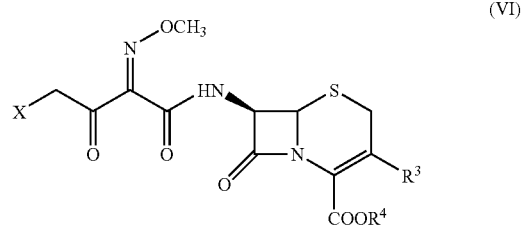

in which:

X is Cl or Br;
R$^4$ is H and
R$^3$ is selected from the group consisting of

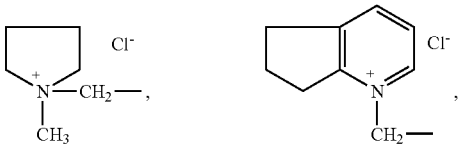

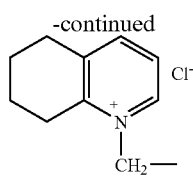

comprising:
(1) reacting a compound of formula (III)

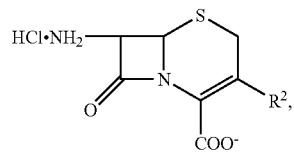
(III)

in which R² is selected from the group consisting of

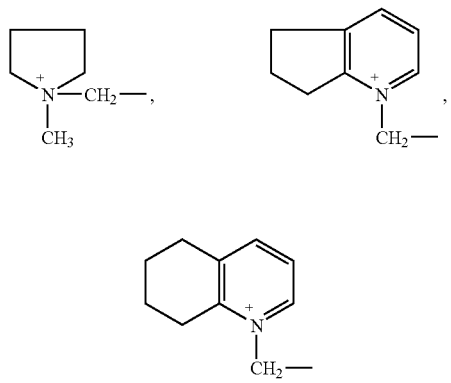

with a trialkylsilyl reactant to form a trialkylsilylester intermediate, (2) reacting said trialkylsilylester intermediate with a compound of formula (V),

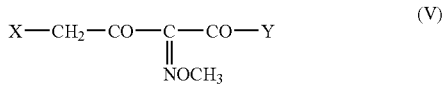
(V)

in which X is Cl or Br, Y is Cl or O—CH=N⁺(CH₃)₂Cl⁻, to obtain a compound of formula (VI')

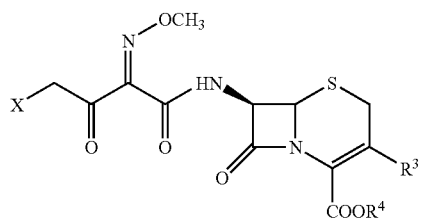
(VI')

in which:
X is Cl or Br;
R⁴ is trialkylsilyl and
R³ is selected from the group consisting of

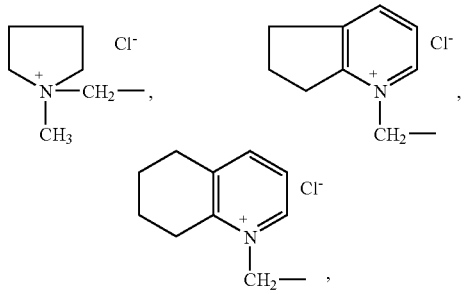

and (3) hydrolyzing the compound of formula (VI') in wet isopropanol to obtain the compound of formula (VI).

2. The process according to claim 1, wherein substituent X in the compound of formula (VI) is Cl.

3. The process according to claim 1, wherein substituent X in the compound of formula (VI) is Br.

4. The process according to claim 1, wherein R³ in the compound of formula (VI) is

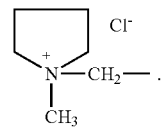

5. The process according to claim 1, wherein R³ in the compound of formula (VI) is

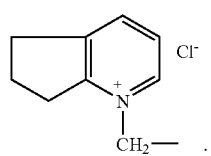

6. The process according to claim 1, wherein R³ in the compound of formula (VI) is

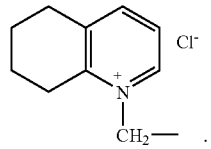

7. The process according to claim 1, wherein the trialkylsilyl reactant of step (1) is N,O-bistrimethyl-silyl-acetamide.

8. The process according to claim 1, wherein Y in the compound of the formula (V) is Cl.

9. The process according to claim 1, wherein Y in the compound of the formula (V) is O—C=N⁺(CH₃)₂Cl⁻.

10. The process according to claim 1, wherein the reaction of step (1) occurs at a temperature ranging from 33 to 35° C.

11. The process according to claim 1, wherein the reaction of step (2) occurs at a temperature ranging from −40 to −35° C.

12. The process according to claim 1, wherein said reacting of said compound of formula (III) with a trialkyl silyl reactant and said reacting of said trialkylsilylester with a compound of formula (V) are carried out in the presence of acetonitrile.

13. The process according to claim 1, further comprising purifying by crystallization said compound of formula (VI) in the presence of isopropanol.

* * * * *